(12) United States Patent
Ducheneaut et al.

(10) Patent No.: US 8,943,419 B2
(45) Date of Patent: Jan. 27, 2015

(54) SYSTEM FOR CREATING COLLABORATIVE CONTENT

(75) Inventors: Nicolas B. Ducheneaut, Sunnyvale, CA (US); Michael Roberts, Los Gatos, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 1172 days.

(21) Appl. No.: 12/417,932

(22) Filed: Apr. 3, 2009

(65) Prior Publication Data
US 2010/0257463 A1    Oct. 7, 2010

(51) Int. Cl.
G06F 3/048     (2013.01)
G06Q 10/10     (2012.01)
A61B 19/00     (2006.01)

(52) U.S. Cl.
CPC ............ *G06Q 10/10* (2013.01); *A61B 19/5244* (2013.01); *A61B 19/52* (2013.01)
USPC ............... 715/757; 715/733; 700/95; 700/96; 700/118

(58) Field of Classification Search
CPC .. G06F 2217/34; G06F 17/50; G06F 17/5004
USPC ................ 715/757; 700/95–98, 118
See application file for complete search history.

(56) References Cited

U.S. PATENT DOCUMENTS

| | | | | |
|---|---|---|---|---|
| 2005/0251462 A1* | 11/2005 | Nykamp | ........................ | 705/27 |
| 2006/0004472 A1* | 1/2006 | Eichstaedt et al. | .............. | 700/96 |
| 2007/0055401 A1* | 3/2007 | Van Bael et al. | ................ | 700/98 |
| 2008/0188969 A1* | 8/2008 | O'Malley et al. | ............... | 700/97 |
| 2010/0010655 A1* | 1/2010 | Corcoran et al. | ............... | 700/98 |
| 2010/0030578 A1* | 2/2010 | Siddique et al. | .................. | 705/3 |

OTHER PUBLICATIONS

Witcomb et al., A Prescriptive Production-Distribution Approach for Decision Making in New Product Design; © 1999; IEEE; 13 pages (336-348).*
Yue et al., Domain-specific Groupware Environment for—esearch on Chemistry, © 2009; IEEE; 6 pages.*

* cited by examiner

*Primary Examiner* — Linh K Pham
(74) *Attorney, Agent, or Firm* — Shun Yao; Park, Vaughan, Fleming & Dowler LLP (57) ABSTRACT

Embodiments of a system, a method, and a computer-program product (e.g., software) for collaboratively generating content from multiple users is described. This system may allow multiple users to create and maintain content that includes a complicated object, including linked spatial and text information, which can include dynamic spatial relationships between components in the complicated object. In particular, the system may receive one or more modifications to content associated with the complicated object from one or more users, and may provide signals to display the modified complicated object in a 3-d space or virtual environment on a display based at least in part on the cumulative modifications.

17 Claims, 6 Drawing Sheets

SYSTEM FOR CREATING COLLABORATIVE CONTENT

BACKGROUND

1. Field

The present disclosure relates to a system and technique for generating and maintaining collaborative content in an interactive multi-dimensional space.

2. Related Art

Online websites that offer collaborative content that is created and maintained by multiple users, such as Wikipedia or other online encyclopedias, are increasingly popular. However, the existing software tools (such as markup languages) used on these websites are often limited to 2-dimensional (2-d) content, such as text, images and video. This limitation can make it difficult for the collaborative content to include accurate and useful representations of complicated objects or complicated technical data. For example, it can be difficult to convey the topography (or "physicality") and function of a four-stroke engine using 2-d images taken from different perspectives or from a 2-d animation of the motion of a piston in the engine. Furthermore, it may also be difficult to convey spatial relationships between components in a complicated object (such as how the components are assembled) or how to diagnose and solve faults using 2-d images or animation.

Interaction among multiple users in 3-dimensional (3-d) virtual environments (which are also referred to as "virtual worlds" or "virtual reality") is also increasingly popular. However, these virtual environments typically only have limited capabilities for displaying and maintaining content from documents. In particular, while a user of such a virtual environment can import and display content from a word processor or presentation tool in an import window, this content is not coupled to other objects in the virtual environment. Consequently, when the user modifies or manipulates the content in the import window, it typically does not affect the remainder of the virtual environment. Thus, while existing virtual environments facilitate interaction among multiple users, they are typically not able to support the collaborative creation and maintenance of content, such as that provided by online encyclopedias.

Hence, what is needed is a method and a system that facilitates the collaborative creation and maintenance of content without the problems listed above.

SUMMARY

One embodiment of the present disclosure provides a system to collaboratively generate content from multiple users. During operation, the system receives a first modification to content associated with an object from a given user in the multiple users, where the content includes text information, spatial image information and one or more two-way links between the text information and the spatial image information. Note that the spatial information includes spatial relationships of components in the object. Then, the system provides first signals to display the modified object in a 3-d space on a display based at least in part on the first modification, where the first signals correspond to a user-selected dynamic representation of the modified object, which includes a current orientation of the modified object in the 3-d space.

Furthermore, the first modification may include: creating at least a portion of the object, which can include creating new text information, new spatial image information or both; changing at least a portion of the object, which can include changing the text information, the spatial image information or both; and/or defining two or more components in the object as a group. For example, the first modification may include defining a given two-way link between a given subset of the text information and the group.

In some embodiments, the content includes: a topic in an online encyclopedia, interactive documentation in an online user manual, and/or temporal image information that defines an animation sequence.

Note that the multiple users may be at different locations in the system and/or may be associated with different organizations. Moreover, the 3-d space may include virtual reality.

Additionally, the spatial image information may include 2- or 3-d image information.

In some embodiments, the system receives a second modification to the content from another user in the multiple users. Then, the system provides second signals to display the modified object in a 3-d space on a display based at least in part on the second modification, where the second signals correspond to a user-selected dynamic representation of the modified object, which includes a current orientation of the modified object in the 3-d space.

In some embodiments, the system includes a computer system, such as a networked computer system.

Another embodiment provides a method including at least some of the above-described operations.

Another embodiment provides a computer-program product for use in conjunction with the computer system.

BRIEF DESCRIPTION OF THE FIGURES

Note that like reference numerals refer to corresponding parts throughout the drawings.

DETAILED DESCRIPTION

The following description is presented to enable any person skilled in the art to make and use the disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not intended to be limited to the embodiments shown, but is to be accorded the widest scope consistent with the principles and features disclosed herein.

Embodiments of a system, a method, and a computer-program product (e.g., software) for collaboratively generating content from multiple users is described. This system may allow multiple users to create and maintain content that includes a complicated object, including linked spatial and text information, which can include dynamic spatial relationships between components in the complicated object. In particular, the system may receive one or more modifications to content associated with the complicated object from one or more users, and may provide signals to display the modified complicated object in a 3-d space or virtual environment on a display based at least in part on the cumulative modifications.

By facilitating an interactive 3-d virtual environment, the system allows the users to convey topography information, spatial relationships and diagnostic information for the complicated object. Moreover, the modifications may include a user-selected dynamic representation of the complicated object, which allows the users to modify a current orientation of the complicated object in the 3-d space. In this way, the system may allow the users to create and maintain useful and accurate representations of complicated objects and/or complicated technical data, for example, in an online encyclopedia or in interactive documentation in an online user manual.

Figure 1:
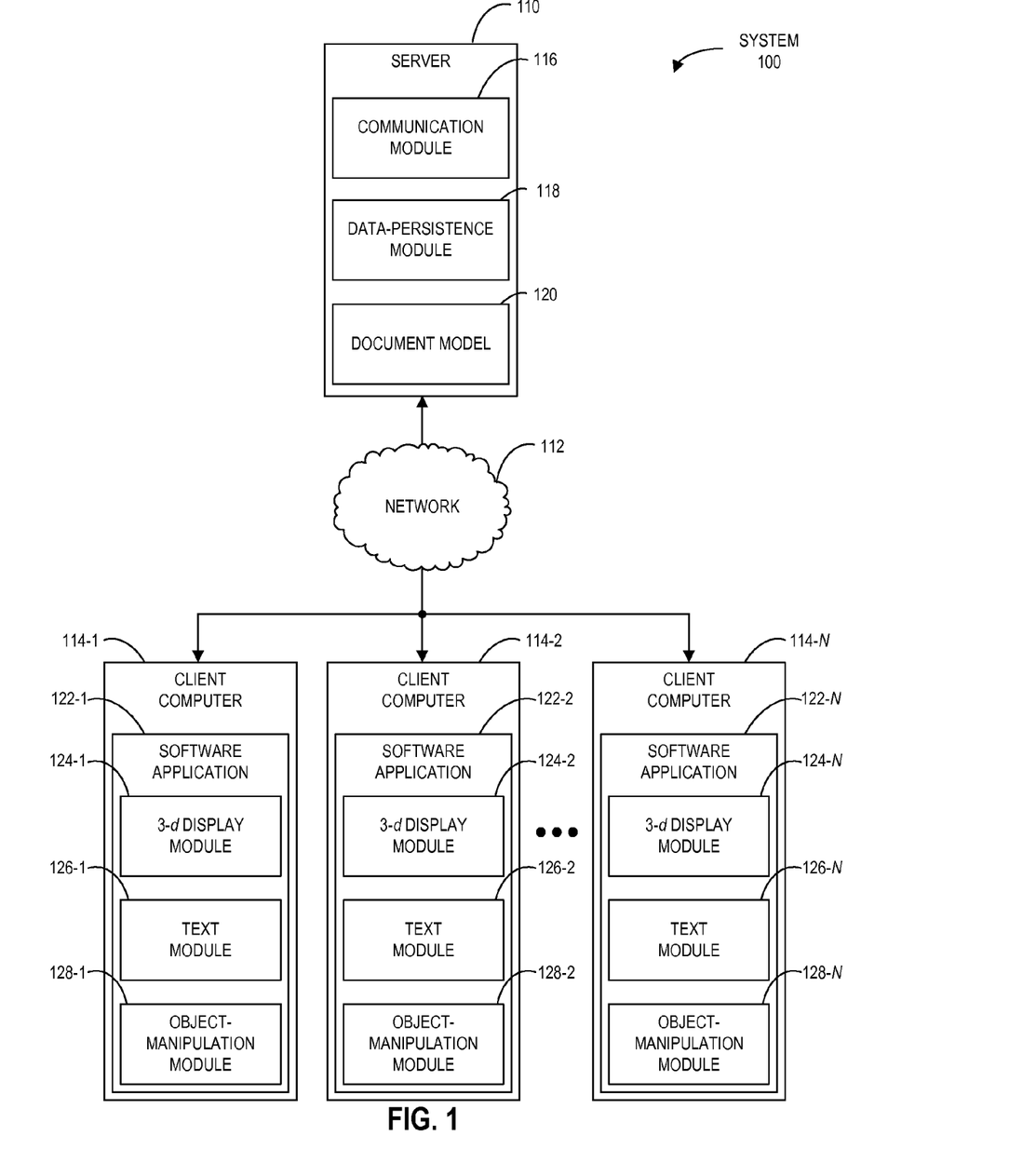
FIG. 1 is a block diagram illustrating a system in accordance with an embodiment of the present disclosure.

We now discuss embodiments of a system to collaboratively generate content from multiple users. FIG. 1 presents a block diagram illustrating a system 100 that implements a client-server architecture. During operation of this system, multiple users of client computers 114 may create and modify content for one or more topics or documents, which are communicated to server 110 via network 112. Note that the users may be at different locations in system 100 and/or may be associated with different organizations. Moreover, the content may be modified by the users over multiple sessions.

Server 110 may store these changes to the content (either locally and/or remotely in system 100), and may provide signals, via network 112, that include the cumulative changes for one or more documents of interest to one or more of the users of client computers 114. These signals may correspond to a 3-d virtual environment, such as virtual reality. When displayed on a given client computer, such as client computer 114-1, this 3-d virtual environment may provide topography information about the spatial information in the one or more documents to a given user. For example, the given user may provide a request to server 110 to change the perspective or orientation of the spatial information and/or the axes in the virtual environment. In response to the request, server 110 may provide revised signals. Furthermore, the content for the given topic may include one or more two-way links between at least a subset of the spatial and text information, which seamlessly integrates both types of information for the users. In this way, the given user may dynamically 'interact' with the content in the virtual environment, such that actions of the given user may modify the content and how it is displayed.

These features may be particularly useful for content such as complicated objects, which include multiple inter-related components or components that have a spatial relationship with each other. For example, using these features the users may be able to collaboratively convey topography information about a complicated object and/or spatial relationships between components in the complicated object. This capability may allow users of system 100 to collaboratively or interactively generate content in applications, such as: an online encyclopedia, an online user manual, remote maintenance, remote training and/or remote surgery.

In the discussion that follows, 3-d content for a complicated object is used as an illustrative example. However, in some embodiments the users may use system 100 to collaboratively create and maintain 2-d content, such as flat text or content that does not include 3-d image information, which can be interactively viewed in the 3-d environment.

Note that the content maintained in system 100 may include a variety of data, including: text, audio, music, images, and/or temporal image information (such as an animation sequence). Moreover, this data may be compatible with a variety of formats, including: image formats (such as a Joint Photographic Experts Group standard), video formats (such as a Moving Pictures Expert Group standard), and word-processing or information-display formats (such as Adobe Acrobat™, from Adobe Systems, Inc. of San Jose, Calif.).

As noted previously, server 110 may provide messaging via a communication module 116 and data persistence via a data-persistence module 118. This allows the remote users to log in, retrieve content for a given document (which, in general, includes both spatial and text information), and store the eventual modifications (if any) that the users make to the given document. Document updates and log in/log out information may be propagated to other active sessions on client computers 114 to enable collaborative editing and social interaction in the context of the given document. Note that data-persistence module 118 ensures that changes to the given document are preserved from one session to the next.

In addition, server 110 provides a document model 120 to represent the major components of the given document and the spatial relationships between them in the 3-d virtual environment. For example, for each document, document model 120 may maintain a list of 3-d components that are to be displayed. This information may include spatial information about the component positions, orientations and scales in the 3-d virtual environment, as well as a pointer to a web page that includes additional information about the components.

In the given document, components may be associated with one or more groups and/or states. For example, the one or more groups may include different types of materials, functions, etc. in a complicated object. The associations between the components in a given group may be defined by the users, such as: 'all screws,' 'outer casing components,' etc. in the complicated object. Furthermore, the components in each group can, in turn, transition from one state to another, e.g., in response to a selection by the given user, the components may change: their position, orientation and/or scale, their material, their color, etc. Thus, the components in a given group may transition from a 'closed' state to an 'open' state, thereby providing an exploded view of the spatial relationships in at least a portion of the complicated object. Consequently, the one or more groups and/or states may allow individual users to create and manipulate components in the complicated object, and to convey relevant spatial and text information about these components.

When creating or modifying the complicated object, the users may use instances of a software application 122 that are resident on and which execute on respective client computers 114. This software application may be a standalone program or may be embedded in another software application. Alternatively, the software application may be a software-application tool that is embedded in a web page (e.g., the software application may execute in a virtual environment provided by a web browser). In an illustrative embodiment, the software-application tool is a software package written in: JavaScript™ (a trademark of Sun Microsystems, Inc.), e.g., the software-application tool includes programs or procedures containing JavaScript instructions, ECMAScript (the specification for which is published by the European Computer Manufacturers Association International), VBScript™ (a trademark of Microsoft, Inc.) or any other client-side scripting language. In other words, the embedded software-application tool may include programs or procedures containing: JavaScript, ECMAScript instructions, VBScript instructions, or instructions in another programming language suitable for rendering by the web browser or another client application on client computers 114.

Note that software application 122 (or software-application tool) may include several modules, including: a 3-d display module 124 (or a viewer), a text module 126, and/or an object-manipulation module 128. 3-d display module 124 may display the spatial information of the given document (such as the various components in the complicated object). User actions (such as mouse clicks) may be recognized by 3-d display module 124, which may have different effects depending on the editing mode in software application 122 (as described further below). Furthermore, 3-d display module 124 may respond to user selection of a link between text and at least a portion of the image information (such as a user-defined group).

By default, text module 126 may display the text information of the given document (e.g., a technical manual explaining how to disassemble the complicated object). For example, when none of the components in the complicated object is selected, text module 126 may display an 'index' page for the entire document.

Then, when the given user selects a component in the displayed spatial information (for example, by clicking on the component using a mouse), text module 126 may display the corresponding text information for the selected component. For example, when the given user clicks on a metal frame in the complicated object, text module 126 may list its: part number, suppliers, price, assembly procedure, etc. Furthermore, each page of text information may be editable (for example, using a what-you-see-is-what-you-get or WYSIWYG editor that may be integrated into software application 122), and the resulting modified content may be saved as Hypertext Markup Language (HTML) and/or eXtensible Markup Language (XML).

Additionally, as noted previously, the given user may insert custom two-way links (from text information-to-spatial information and from spatial information-to-text information) into the given document, such as on one or more pages. These links may couple or associate text information on these pages with corresponding portions or components in the displayed spatial information for the complicated object. For example, a given link may cause a group of components to be selected. Alternatively or additionally, the given link may cause the same group to transition from one state to another (such as from an 'open' state to a 'closed' state, as illustrated further below in FIGS. 3A and 3B).

Object-manipulation module 128 may be used to: position components, group them, and/or define transitions between states. For example, the user may click on tabs in a window in a user interface in order to switch the editing mode (and thus the view in software application 122) between: movement, tagging, and grouping/states. During the movement-editing mode, the position, orientation and/or scale of the components and/or complicated objects may be arbitrarily adjusted in the 3-d space based on the given users' desired intent. Moreover, during the tagging editing mode, tags associated with each component in the complicated object may be displayed in proximity, which facilitates the identification of key components by other users. Users may add new tags or modify existing tags, and save their changes by activating an icon (which initiates communication with data-persistence module 118) for future viewing or use.

Additionally, during the grouping/states editing mode, several components can be selected simultaneously. The resulting group can be given a name, which can then be displayed as a link in the displayed text information to allow users to easily select the group subsequently. Components in a given group may be moved, rotated and/or scaled by users using the movement-editing mode described previously. Similarly, the resulting state(s) can be named and saved (e.g., a 'top cover' group may have an 'unscrewed' state and a 'screwed-on' state). These states can, in turn, be displayed as a link in the displayed text information to allow users to easily select a particular state of the group of components. When the link for a given state is selected by the given user, it may cause the displayed spatial information for the components to transition, thereby visually illustrating the corresponding actions or operations described in the text information.

Figure 2:
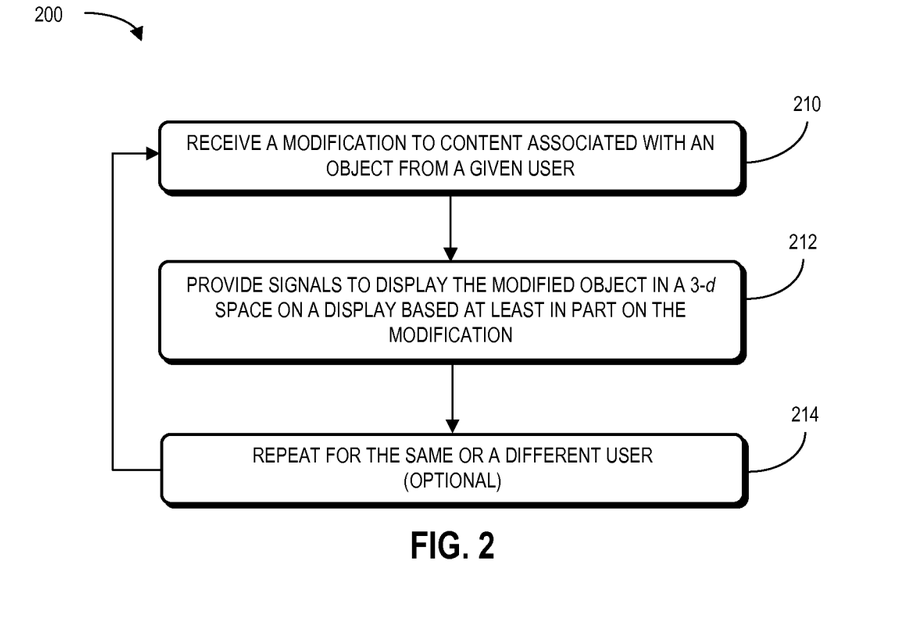
FIG. 2 is a flow chart illustrating a process for collaboratively generating content from multiple users in accordance with an embodiment of the present disclosure.

We now discuss embodiments of a process for collaboratively generating content from multiple users. FIG. 2 presents a flow chart illustrating a process 200 for collaboratively generating content from multiple users, which may be performed by a system (such as system 100 in FIG. 1). During operation, the system receives a modification to content associated with an object from a given user in multiple users (210), where the content includes text information, spatial image information and one or more two-way links between the text information and the spatial image information. Note that the spatial information includes spatial relationships of components in the object. Then, the system provides signals to display the modified object in a 3-d space on a display based at least in part on the modification (212), where the signals correspond to a user-selected dynamic representation of the modified object, which includes a current orientation of the modified object in the 3-d space.

Note that the modification may include: creating at least a portion of the object, which can include creating new text information, new spatial image information or both; changing at least a portion of the object, which can include changing the text information, the spatial image information or both; and/or defining two or more components in the object as a group. For example, the modification may include defining a given two-way link between a given subset of the text information and the group.

Note that process 200 may include additional or fewer operations. For example, the operations of receiving the modification (210) and providing signals to display the modified object (212) may be optionally repeated (214) multiple times for the same user and/or for one or more other users in the multiple users. Moreover, the order of the operations may be changed and/or two or more operations may be combined into a single operation.

Figure 3A:
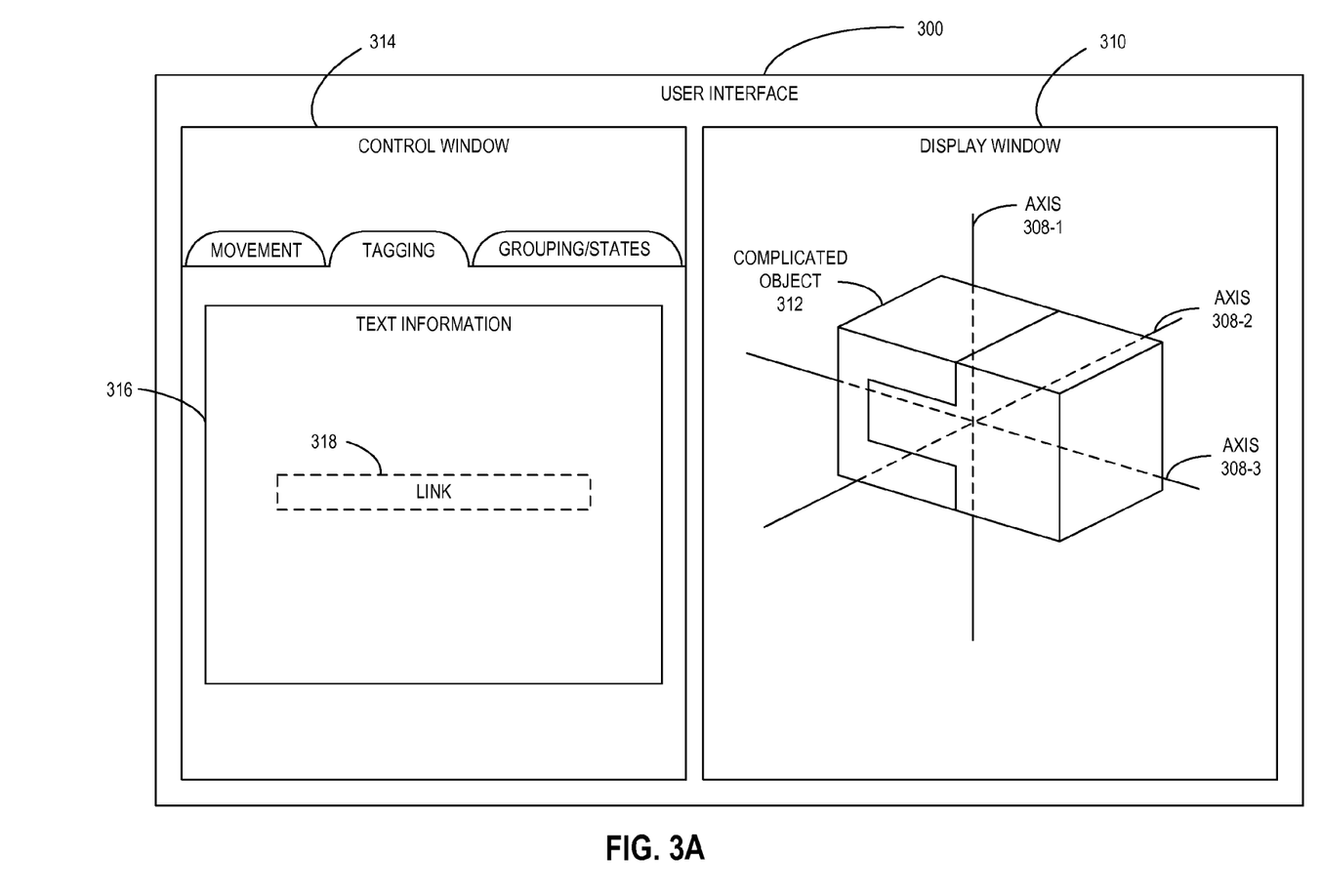
FIG. 3A is a drawing of a user interface in accordance with an embodiment of the present disclosure.

We now describe embodiments of a user interface in software application 122 (FIG. 1). FIG. 3A presents a drawing of a user interface 300. In this user interface, display window 310 displays spatial information for complicated object 312 in the virtual environment (with axes 308) based at least in part on a current user-selected perspective or orientation. Using a mouse, a user may select a component or group of components in complicated object 312, in which case text information 316 associated with the selected component(s) may be displayed in control window 314.

In addition, control window 314 includes multiple tabs that allow a user to select one of the previously described editing modes, including: movement, tagging, and grouping/states. These editing modes can be used to define spatial and text information for new components and/or to modify the spatial and text information for existing components. Furthermore, during the grouping/states editing mode, existing groups of components and/or their associated states can be viewed in control window 314, and new groups of components and/or their associated states can be defined. When a group or state is defined, a two-way link (such as link 318) may be included in the associated text information in window 314.

If the user clicks on link 318 using a mouse, the spatial information for complicated object 312 may transition from a first state (such as a 'closed' state) to a second state (such as an 'open' state). Alternatively, the user may right click on a group in complicated object 312 in display window 310, and may then select the state in a pop-up window that is displayed.

Figure 3B:
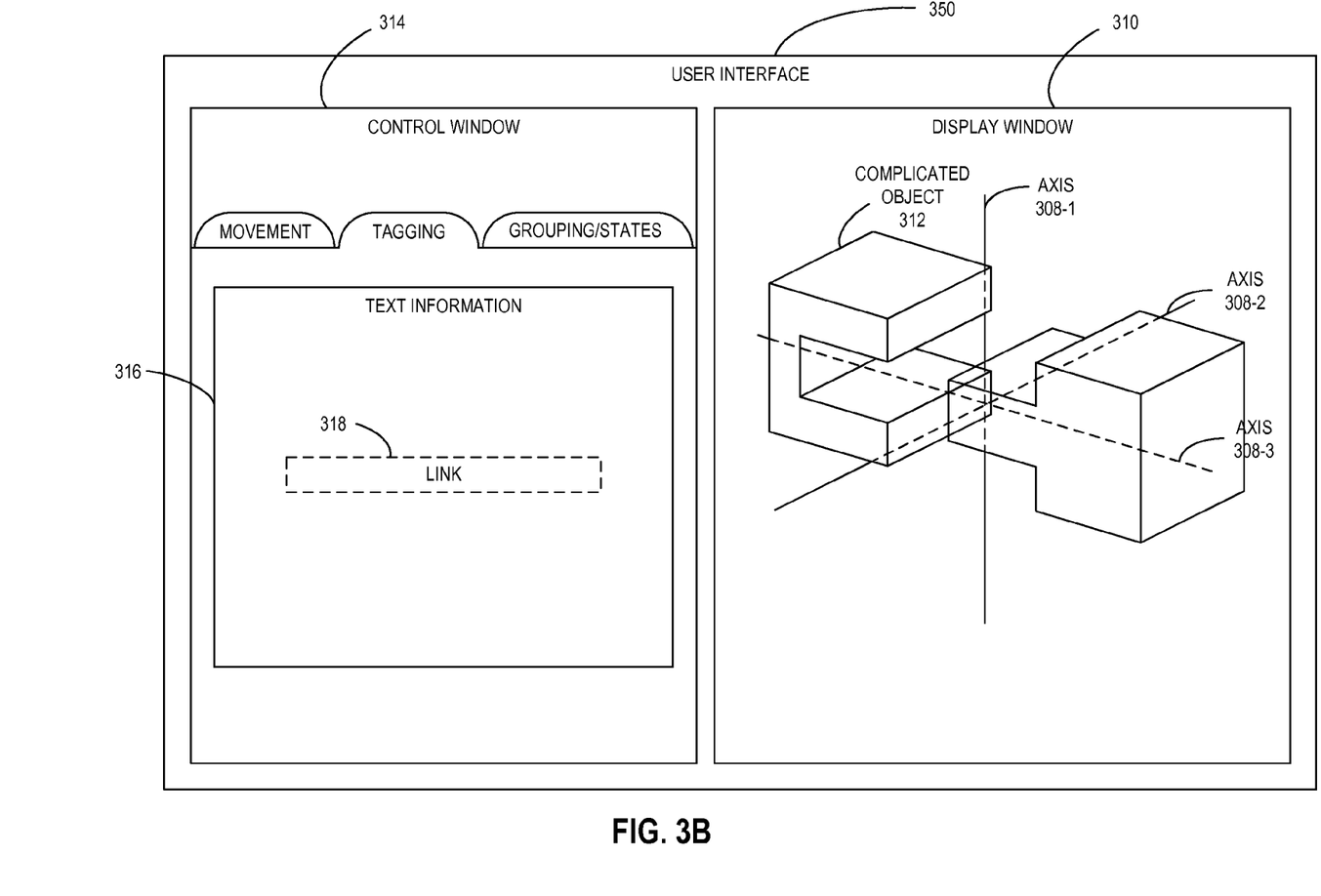
FIG. 3B is a drawing of a user interface in accordance with an embodiment of the present disclosure.

A transition to an 'open' state (from the closed state shown FIG. 3A) is shown in FIG. 3B, which presents a drawing of a user interface 350. Note that the exploded or open view of the components in complicated object 312 visually illustrate the corresponding actions or operations (and more generally, the information) described in text information 316. In some embodiments, activating a link (such as link 318) may initiate an animated sequence of temporal image information in display window 310.

In an exemplary embodiment, system 100 (FIG. 1) and process 200 (FIG. 2) are used to generate 'interactive documentation.' Many existing user manuals for complicated technical products (e.g., a copy machine) are both hard to use and static. This is because 'flat' paper usually does not convey the structure or topography of a machine easily, which can make following diagnosis and problem-solving procedures difficult. Moreover, as new issues and fixes are discovered, the manual needs to be edited and reprinted, which can be costly and takes time to propagate back to users.

The system and technique described herein addresses these challenges by transforming a product manual into an interactive text and spatial environment that can be edited and preserved. End users can use such a dynamic and intuitive product manual for troubleshooting. This may increase the ease of use of the product, which in turn may increase customer satisfaction. This approach to a product manual also has the potential to reduce the number of technician visits to customer sites, with commensurate cost savings.

Furthermore, the dynamic and intuitive product manual can also be used by technicians for knowledge sharing. As new problems and solutions are discovered in the field, technicians can document precisely the operations leading to the problem and how to address it. This cumulative knowledge can be presented to other technicians the next time they log in.

Additionally, the dynamic and intuitive product manual can be used for training and remote problem solving. Many corporations and organizations suffer from a so-called 'knowledge gap,' in which a few technicians/designers are intimately familiar with the inner workings of a machine, and a much larger but also less-qualified group is tasked with maintaining and fixing these machines in the field. This poses a so-called 'reachback' problem. When faced with a technical issue, technicians in the less-qualified group many not be able to solve this by themselves. Instead, these technicians typically may contact an expert, who provides guidance. When such consultations are typically performed over the phone or via email, it may be extremely difficult for the expert to explain complex procedures that are much more easily understood visually. If the problem cannot be solved this way, then the expert may need to travel to the customer site or the malfunctioning machine may have to be shipped back to the expert, either of which is time consuming and expensive.

The system and technique described herein addresses this problem by allowing field technicians and experts to log in and interact in the 3-d space provided by the virtual environment, where the experts can train the technicians to perform the necessary procedure(s). The topographic information in the virtual environment makes it easier for the experts to explain how to manipulate the components in a machine. Moreover, as the training session takes place, the expert can document the procedure(s) using text, groups, and states, and can save the final result. This enables asynchronous learning and teaching, because future users will be able to learn the procedure(s) without the expert being present.

Figure 4:
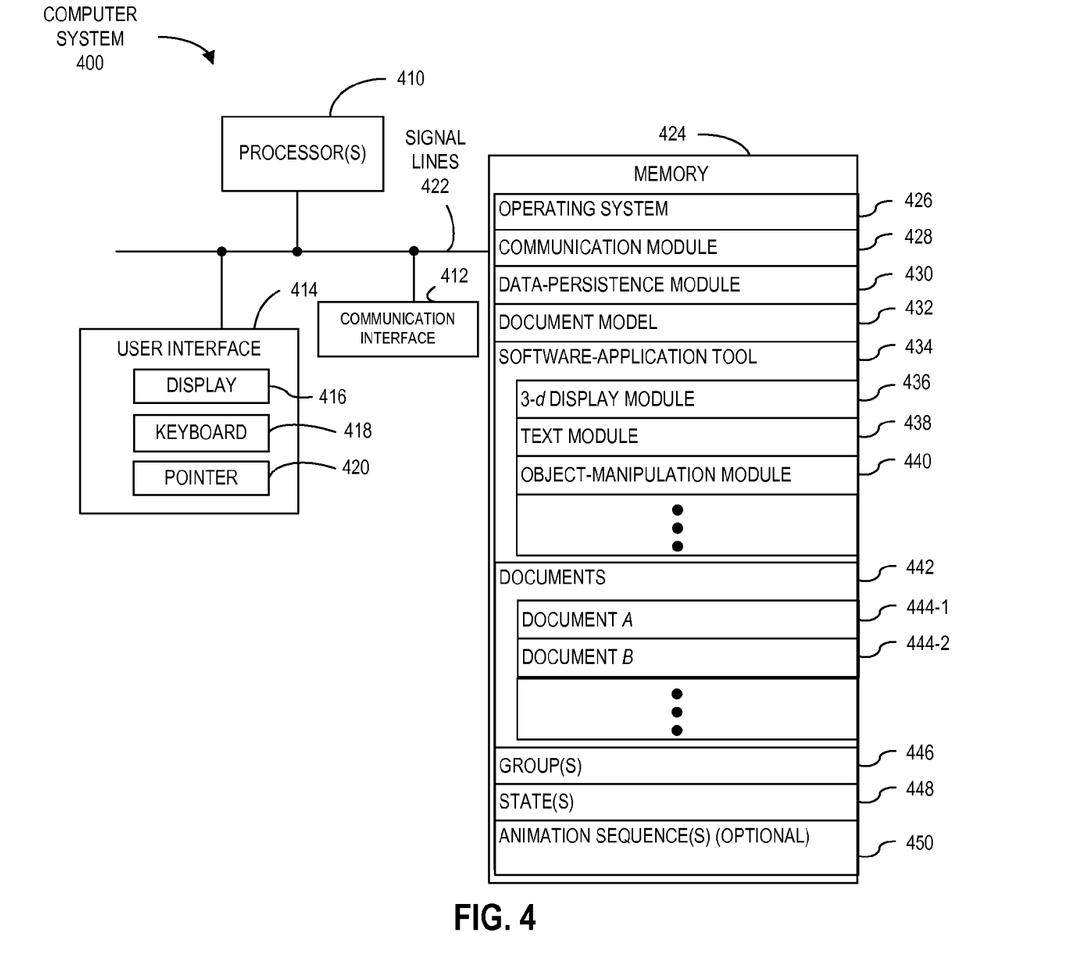
FIG. 4 is a block diagram illustrating a computer system in accordance with an embodiment of the present disclosure.

We now further describe embodiments of a computer system (which may be included in system 100 in FIG. 1) that performs process 200 (FIG. 2). FIG. 4 presents a block diagram illustrating a computer system 400. Computer system 400 includes: one or more processors 410, a communication interface 412, a user interface 414, and one or more signal lines 422 coupling these components together. Note that the one or more processing units 410 may support parallel processing and/or multi-threaded operation, the communication interface 412 may have a persistent communication connection, and the one or more signal lines 422 may constitute a communication bus. Moreover, the user interface 414 may include: a display 416, a keyboard 418, and/or a pointer 420, such as a mouse.

Memory 424 in the computer system 400 may include volatile memory and/or non-volatile memory. More specifically, memory 424 may include: ROM, RAM, EPROM, EEPROM, flash, one or more smart cards, one or more magnetic disc storage devices, and/or one or more optical storage devices. Memory 424 may store an operating system 426 that includes procedures (or a set of instructions) for handling various basic system services for performing hardware-dependent tasks. In some embodiments, the operating system 426 is a real-time operating system. While not shown in FIG. 4, in some embodiments memory 424 includes a web browser. Memory 424 may also store communication procedures (or a set of instructions) in a communication module 428. These communication procedures may be used for communicating with one or more computers, devices and/or servers, including computers, devices and/or servers that are remotely located with respect to the computer system 400.

Memory 424 may also include multiple program modules (or sets of instructions), including: data-persistence module 430 (or a set of instructions), document model 432 (or a set of instructions), and/or software-application tool 434 (or a set of instructions). Moreover, software-application tool 434 may include: 3-d display module 436 (or a set of instructions), text module 438 (or a set of instructions), and/or object-manipulation module 440 (or a set of instructions).

As described previously, users of software-application tool 434 may define and modify text and spatial information for documents 442, such as document A 444-1 and document B 444-2, using text module 438 and object-manipulation module 440. For example, users may define one or more groups 446, states 448 and/or optional animation sequences 450. The resulting cumulative content may be interactively displayed by display module 436 based on instructions or signals from document model 432 that are communicated by communication module 428. In addition, data-persistence module 430 may maintain a record of any modifications or changes for future use by the users.

Instructions in the various modules in memory 424 may be implemented in: a high-level procedural language, an object-oriented programming language, and/or in an assembly or machine language. This programming language may be compiled or interpreted, i.e., configurable or configured, to be executed by the one or more processing units 410.

Although computer system 400 is illustrated as having a number of discrete items, FIG. 4 is intended to be a functional description of the various features that may be present in computer system 400 rather than a structural schematic of the embodiments described herein. In practice, and as recognized by those of ordinary skill in the art, the functions of the computer system 400 may be distributed over a large number of devices or computers, with various groups of the devices or computers performing particular subsets of the functions. In some embodiments, some or all of the functionality of computer system 400 may be implemented in one or more application-specific integrated circuits (ASICs) and/or one or more digital signal processors (DSPs).

Computers and servers in computer system 400 may include one of a variety of devices capable of manipulating computer-readable data or communicating such data between two or more computing systems over a network, including: a personal computer, a laptop computer, a mainframe computer, a portable electronic device (such as a cellular phone or PDA), a server and/or a client computer (in a client-server architecture). Moreover, network 112 (FIG. 1) may include: the Internet, World Wide Web (WWW), an intranet, LAN, WAN, MAN, or a combination of networks, or other technology enabling communication between computing systems.

In some embodiments, system 100 (FIG. 1), user interface 300 (FIG. 3A), user interface 350 (FIG. 3B) and/or computer system 400 include fewer or additional components. Moreover, two or more components may be combined into a single component and/or a position of one or more components may be changed. Moreover, the functionality of system 100 (FIG. 1), user interface 300 (FIG. 3A), user interface 350 (FIG. 3B) and/or computer system 400 may be implemented more in hardware and less in software, or less in hardware and more in software, as is known in the art.

Figure 5:
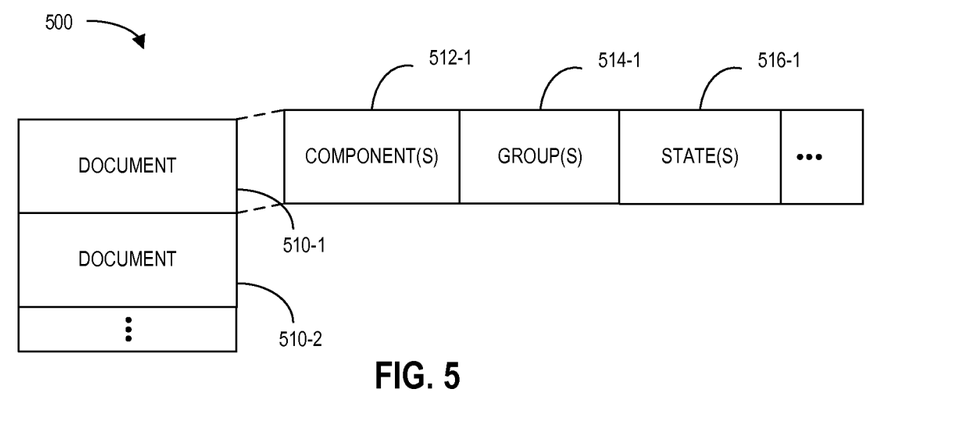
FIG. 5 is a block diagram illustrating a data structure in accordance with an embodiment of the present disclosure.

We now discuss data structures that may be used in computer system 400. FIG. 5 presents a block diagram illustrating a data structure 500. This data structure may contain content for one or more documents 5 10. For example, document 510-1 may include: one or more components 512-1, one or more groups 514-1, and/or one or more states 516-1. Moreover, the information in document 510-1 may include text and spatial information, such as positions, orientations and sizes for components 512-1, as well as one or more two-way links between the text and the spatial information.

In some embodiments, data structure 500 includes fewer or additional components. Moreover, two or more components may be combined into a single component and/or a position of one or more components may be changed.

The foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art. Additionally, the above disclosure is not intended to limit the present disclosure. The scope of the present disclosure is defined by the appended claims.

What is claimed is:

1. A method for collaboratively generating publicly accessible content from multiple users of a networked computer system, comprising:
   receiving, in a movement editing mode, a first manipulation to a 3-dimensional representation of a physical object from a given user of the multiple users;
   receiving, in a tagging editing mode, a second manipulation to a textual tag of the 3-dimensional representation from a given user of the multiple users, wherein the second manipulation comprises one or more of: adding a new tag, modifying an existing tag; and saving a tag;
   adjusting the 3-dimensional representation to incorporate the first and second manipulations;
   receiving, in the movement editing mode, a third manipulation to an animation sequence of the 3-dimensional representation from another user of the multiple users;
   adjusting the 3-dimensional representation to incorporate the third manipulation; and
   publicly publishing and displaying the adjusted 3-dimensional representation in a 3-dimensional space on a display.

2. The method of claim 1, wherein the multiple users are at different locations in the networked computer system.

3. The method of claim 1, wherein the multiple users are associated with different organizations.

4. The method of claim 1, wherein the first manipulation includes creating at least a portion of the 3-dimensional representation.

5. The method of claim 1, wherein the first manipulation includes changing at least a portion of the 3-dimensional representation.

6. The method of claim 1, wherein the first manipulation includes defining two or more components in the 3-dimensional representation as a group.

7. The method of claim 1, wherein the 3-dimensional space includes publicly accessible virtual reality.

8. The method of claim 1, wherein the content includes a topic in an online encyclopedia.

9. The method of claim 1, wherein the content includes interactive documentation in an online user manual.

10. The method of claim 1, wherein the animation sequence is a publicly accessible animation sequence, and wherein the content includes temporal information of the 3-dimensional representation that defines the publicly accessible animation sequence.

11. The method of claim 1, further comprising receiving a selection for an editing mode from a set of editing modes comprising the movement editing mode, the tagging editing mode, and a grouping/states editing mode.

12. A computer-program product for use in conjunction with a computer system, the computer-program product comprising a non-transitory computer-readable storage medium and a computer-program mechanism embedded therein to collaboratively generate content from multiple users of a networked computer system, the computer-program product including:
   instructions for receiving, in a movement editing mode, a first manipulation to a 3-dimensional representation of a physical object from a given user of the multiple users;
   instructions for receiving, in a tagging editing mode, a second manipulation to a textual tag of the 3-dimensional representation from a given user of the multiple users, wherein the second manipulation comprises one or more of: adding a new tag, modifying an existing tag; and saving a tag;
   instructions for adjusting the 3-dimensional representation to incorporate the first and second manipulations;
   instructions for receiving, in the movement editing mode, a third manipulation to an animation sequence of the 3-dimensional representation from another user of the multiple users;
   instructions for adjusting the 3-dimensional representation to incorporate the third manipulation; and
   instructions for publicly publishing and displaying the adjusted 3-dimensional representation in a 3-dimensional space on a display.

13. The computer-program product of claim 12, wherein the multiple users are associated with different organizations.

14. The computer-program product of claim 12, wherein the animation sequence is a publicly accessible animation sequence, and wherein the content includes temporal information of the 3-dimensional representation that defines the publicly accessible animation sequence.

15. The computer-program product of claim 12, wherein the content includes a topic in an online encyclopedia.

16. The computer-program product of claim 12, further comprising instructions for receiving a selection for an editing mode from a set of editing modes comprising the movement editing mode, the tagging editing mode, and a grouping/states editing mode.

17. A computer system, comprising:
a processor device;
a memory device;
a program module, wherein the program module is stored in the memory and configured to be executed by the processor, the program module to collaboratively generate content from multiple users of a networked computer system, the program module including:
instructions for receiving, in a movement editing mode, a first manipulation to a 3-dimensional representation of a physical object from a given user of the multiple users;
instructions for receiving, in a tagging mode, a second manipulation to a textual tag of the 3-dimensional representation from a given user of the multiple users, wherein the second manipulation comprises one or more of: adding a new tag, modifying an existing tag; and saving a tag;
adjusting the 3-dimensional representation to incorporate the first and second manipulations;
instructions for receiving, in the movement editing mode, a third manipulation to an animation sequence of the 3-dimensional representation from another user of the multiple users;
instructions for adjusting the 3-dimensional representation to incorporate the third manipulation; and
instructions for publicly publishing and displaying the adjusted 3-dimensional representation in a 3-dimensional space on a display.

* * * * *